United States Patent [19]

Drucker et al.

[11] Patent Number: 5,464,982
[45] Date of Patent: Nov. 7, 1995

[54] RESPIRATORY GAS ANALYZER

[75] Inventors: Steven Drucker, Oakland; Alexey Goder, El Cerrito; Davood Khalili, Santa Clara; Kevin Williams, Pinole; Ken Christensen, Livermore; Emery Major, Point Richmond, all of Calif.

[73] Assignee: Andros Incorporated, Berkeley, Calif.

[21] Appl. No.: 215,481

[22] Filed: Mar. 21, 1994

[51] Int. Cl.⁶ .......................... G01N 21/61; G01N 21/35
[52] U.S. Cl. .................. 250/343; 250/345; 250/339.03; 250/339.04; 250/339.13
[58] Field of Search ...................... 250/339.12, 339.13, 250/343, 345, 346, 349, 353, 252.1 A, 339.01, 339.03, 339.04

[56] References Cited

U.S. PATENT DOCUMENTS

| | | | |
|---|---|---|---|
| 4,618,771 | 10/1986 | Farren | 250/345 X |
| 5,092,342 | 3/1992 | Hattendorff et al. | 250/343 X |
| 5,095,913 | 3/1992 | Yelderman et al. | 250/345 X |
| 5,206,511 | 4/1993 | Apperson et al. | 250/345 X |
| 5,254,858 | 10/1993 | Wolfman et al. | 250/353 X |

FOREIGN PATENT DOCUMENTS

| | | | |
|---|---|---|---|
| 9118279 | 11/1991 | WIPO | 250/345 |

*Primary Examiner*—Constantine Hannaher
*Assistant Examiner*—Edward J. Glick
*Attorney, Agent, or Firm*—Coudert Brothers

[57] ABSTRACT

An improved apparatus and method for measuring the concentration of carbon dioxide in respiratory gases. The apparatus is a non-dispersive gas analyzer attached in series with the respiratory airway which is universally compatible with any host system. The analyzer includes a housing which supports a sample cell containing the respiratory gases, and which contains an infrared radiation source encased in shock absorbing material, means for directing the radiation into a collimated beam path through the sample cell, means for splitting the beam path and directing it towards a pair of infrared detectors for measuring the amount of absorption of carbon dioxide in the sample cell. The analyzer is further improved by the use of two heating servos, one for regulating the temperature of the sample cell windows in order to inhibit condensation build-up and one for regulating the ambient temperature surrounding the detectors so as to ensure more accurate measurements. Calibration means is included within the analyzer housing for storing and providing information characterizing performance parameters of the analyzer.

16 Claims, 4 Drawing Sheets

RESPIRATORY GAS ANALYZER

FIELD OF THE INVENTION

This invention relates generally to non-dispersive infrared spectrophotometers. More particularly, this invention relates to an improved gas analyzer which measures the concentration of carbon dioxide in respiratory gases present in a sample cell which is in series with the airway of a patient.

BACKGROUND OF THE INVENTION

Gas analyzers of the non-dispersive type typically operate on the premise that the concentration of a designated gas can be measured: (1) by passing a beam of infrared radiation through the gas, and (2) ascertaining the attenuation of the energy in a narrow wavelength band absorbable by the designated gas with a detector capable of generating an electrical output signal proportioned to the energy in the band passing through the gas. Examples of such analyzers are disclosed in U.S. Pat. Nos. 4,859,858, 4,859,859, 4,914,720, and 5,092,342.

Medical applications of these gas analyzers include the monitoring of end-tidal carbon dioxide, i.e., the concentration of carbon dioxide in a patient's exhalations. This expired carbon dioxide level can be employed by medical personnel to monitor the operation of a mechanical ventilator hooked up to the patient to assist him or her in breathing. In one typical arrangement, a system consisting of a nasal cannula through which the patient exhales can be employed so that expired breath is transmitted through a line to the gas analyzer. An example of a prior art device employing a nasal cannula is shown and described in U.S. Pat. No. 4,958,075.

In a typical medical application of a gas measuring apparatus for measurement of blood gases, a replaceable or interchangeable sample cell or cuvette is employed to connect a tube inserted into the patient's trachea to the plumbing of a mechanical ventilator. The sample cell confines the expired gases to a flow path with a precise, transverse dimension, and it furnishes an optical path between an infrared radiation emitter and an infrared radiation detector unit, both components of a gas analyzer "bench".

The infrared radiation traverses the gases in the sample cell adaptor where it is attenuated because part of the radiation is absorbed by the designated gas being analyzed. The attenuated beam of infrared radiation is then filtered to eliminate energy of frequencies lying outside the narrow band absorbed by the gas being measured. The infrared radiation in that band impinges upon a detector which consequently generates an electrical signal proportional in magnitude to the intensity of the infrared radiation impinging upon it.

The prior art systems disclosed in U.S. Pat. Nos. 4,859,858, 4,859,859, 4,914,720, 4,958,075, and 5,092,342 each include a gas analyzer and a disposable sample cell or cuvette. The sample cell is designed to be inserted into the airway of a patient on a ventilator and includes a pair of opposed windows having a line of sight positioned transverse to the sample cell so as to allow a beam of infrared radiation to pass therethrough. The sample cell is designed to be placed into the sensor unit so that the windows are in alignment with the beam path of the infrared source described above.

The gas analyzer systems disclosed in U.S. Pat. Nos. 4,859,858, 4,859,859, and 4,914,720 measure the carbon dioxide content in a respiratory gas. The respiratory gas flows through a sample cell through which an infrared beam is directed. The radiation originates from a pulsed infrared radiation source and is directed by a parabolic mirror. The mirror collimates the radiation emitted into a beam of parallel rays and focuses this beam along an optical path through the sample cell and directly onto an infrared sensitive detector located downstream of the cell. The beam is attenuated as it transverses the gas mixture because part of the radiation is absorbed by the $CO_2$ gas. The detector measures the amount of attenuation caused to the infrared beam by the respiratory gas. The amount of attenuation corresponds to the concentration of $CO_2$ in the respiratory gas.

To improve the sensitivity of the detector disclosed in the '859 patent, an optical filter is incorporated in front of the detector to pass a narrow band of only those wavelengths of infrared radiation absorbed by the $CO_2$. A wavelength of approximately 4.3 microns is conventionally selected for this purpose. The remaining infrared radiation in the band impinges upon the detector. The detector then generates an electrical signal proportional in magnitude to the intensity of the infrared radiation impinging upon it, i.e., the concentration of $CO_2$.

To increase the accuracy in measuring $CO_2$ concentration, a second detector-filter pair is employed which is positioned juxtaposed or adjacent to the first detector-filter pair. The second filter is designed to pass a similar narrow band of infrared radiation of a wavelength that is not absorbed by the $CO_2$. This second band of infrared radiation typically has a wavelength of approximately 3.7 microns and is adjacent to the band of absorbable radiation. The second detector also generates an electrical signal but one that is proportional to the magnitude of the radiation not absorbed by the $CO_2$.

The output signals generated by the detectors are sent to the signal processor. The signals are ratioed to eliminate errors in the measured concentration of the $CO_2$. These errors are attributable to such factors as foreign substances (e.g., condensation on the cuvette windows) and other instabilities in the infrared source and/or the detectors.

The gas analyzer disclosed in the '342 patent employs the above dual detector-filter pair but adds two additional components, a beam splitter and a lens configuration, to increase the sensitivity and accuracy of the detectors. A dichroic beam splitter is incorporated in the beam path ahead of the detectors. This beam splitter separates the two wavelengths to be measured out of the radiation spectrum and directs only the preselected wavelength to its corresponding detector. More specifically, the dichroic beam splitter is made of a material which transmits infrared radiation having a wavelength of 3.7 microns and permits the rays of this wavelength to impinge upon the "reference" detector. On the other hand, rays having a radiation wavelength of 4.3 microns are reflected and directed to the "measuring" detector. The added lens configuration consists of a lens positioned in front of the beam splitter which focuses the beam, after it passes through the sample cell, onto the detectors. Both of these additional features reduce the detector inaccuracy due to an obscured optical path caused by condensation and foreign particles on the cuvette windows.

One disadvantage of this lens configuration is the heightened possibility of dissymmetry between the two preselected wavelength beam paths caused by the cumulative effect of lens tolerance error. In other words, even a minor tolerance error produced by obstruction of the optical path is multiplied by some factor as the obscured beam is focused by each lens. Especially if the error is present in only one of the beam paths, the resulting dissymmetry between the two paths gives a less accurate $CO_2$ concentration measurement.

Therefore, it is desirable to design a gas analyzer which accurately focuses the beams of selected wavelengths without increasing dissymmetry between the two selected beam paths. The present invention proposes to accomplish this by an improved lens-free design. In addition to aiding in the symmetry of the detector measurements, the elimination of the lenses makes for a less expensive and lighter weight unit.

Again referring to the prior art systems disclosed in U.S. Pat. Nos. 4,859,858, 4,859,859, and 4,194,720, because of the juxtaposition of the two detectors, the infrared radiation reaching both detectors will, for all practical purposes, be attenuated equally by condensation on the sample cell windows and contamination along the optical path between the infrared radiation emitter and the detectors. Also, it will be equally affected by thermal drift and variations in the ambient temperature. To help eliminate any error caused by condensation, contamination, thermal drift or ambient temperature variations, the signals generated by the detectors are ratioed.

The above prior art systems preferably employ lead selenide detectors for their high sensitivity and comparably low cost. However, lead selenide detectors are very temperature sensitive with temperature variation affecting the bulk resistivity and the sensitivity of the detector material. Errors that would be produced by variations in detector temperature cannot be eliminated by employing the ratioing technique discussed above. In fact, the signal from the infrared radiation detector can be lost, despite ratioing, if the detector temperature varies as little as 0.1° C. Therefore, to maintain the detectors at a constant and precise temperature, a detector heater arrangement is provided in addition to employing the ratioing technique. This heating of the detectors also keeps unwanted condensation from forming on the optical components of the assembly in which the detectors are incorporated.

This prior art heating arrangement employs a strip heater of conventional construction and a thermistor for sensing the temperature in the detector unit. Both the strip heater and the thermistor are juxtaposed adjacent and in intimate heat transfer relationship to the detector and the housing or casing of the detector unit. The thermistor sends an analog signal to temperature control circuitry which converts that signal into digital form. This digital temperature signal is utilized in a feedback loop to control the duty cycle of the strip heater.

The disadvantage of this heating arrangement is that the sample cell windows can only by heated indirectly by means of heat transfer from the detector unit. Thus, condensation on the sample cell windows is not effectively evaporated.

In lieu of the above-described heating arrangement, other prior art arrangements employ a sample cell window heating system. For example, U.S. Pat. No. 5,092,342 discloses gas analyzer wherein electrical heating elements are applied directly to the surface of one or both of the sample cell holder windows on the respective sides facing away from the sample cell. Several electrically conductive band or track configurations are disclosed wherein the beam path is unobstructed. The heated windows are in a virtual touching contact engagement with the sample cell when the latter is seated in the gas analyzer bench so as to allow for a good heat transfer from the band to the sample cell windows. In this way, the condensation of water vapor which can occur on the inner surface of the sample cell windows is avoided.

A heat transfer relationship also exists between the detector assembly and the sample cell window closest to it. For this purpose, the block containing the detector is made of a thermally-conductive material. A temperature sensor embedded in the detector block or positioned between the block and the heated window is employed to control the temperature of the gas analyzer.

This heating arrangement is limited, however, in that the temperature of the detector block and the sample cell window(s) are dependent upon each other. In other words, there is only one source of heat, i.e, the window heaters, and one temperature sensor for both.

The prior art systems disclosed in U.S. Pat. Nos. 4,859,858, 4,859,859 and 4,194,720 each include a hand-held unit, remote from the gas analyzer bench, which contains all the electronic control, processing and power circuitry of the device. With this design, the electronic circuitry is housed remote from bench components. The remote unit holds a microcomputer, an analog-to-digital converter, signal processing circuitry and power supply circuitry. The microcomputer controls the operation of the infrared emitter, a heater which keeps the detectors at a constant, precise temperature, and the displays of a variety of information concerning the gas being measured. The analog-to-digital converter converts the signal emitted by the detectors to a ratioed signal indicative of the concentration of $CO_2$ in the respiratory gas sample. The signal processing circuitry controls the operation of the gas analyzer and processes the detector-generated signals to display such medically-relevant information as minimum inspired $CO_2$, respiration rate, and end tidal $CO_2$, in addition to instantaneous concentration of $CO_2$.

By locating the system's control circuitry remote from the gas analyzer bench, the above systems have the disadvantage of being required to use the same bench with the same hand-held electronics unit. This matching is necessary because each gas analyzer's infrared source, detector(s) and filter(s) have unique operating specifications and performance characteristics which are accommodated for by the companion electronics unit. The lack of interchangeability between the bench and electronics requires a user to use caution in pairing a bench with its corresponding electronic unit to avoid a calibration mismatch. Even if such a system provided interchangeable benches, information characterizing the individual gas analyzer's performance must be available to the processing means if the host monitor is to accurately interpret the signals from the detector(s). This would require the gas analyzer to be calibrated each time it is plugged into a corresponding host unit.

Furthermore, these systems are cumbersome due to the plurality of components, i.e., gas analyzer bench, electronics unit, and interconnecting cable. There is also the additional disadvantage of the distortion and noise attributable to the transmission of electronic signals via an external cable.

Therefore, it is desirable to design a gas analyzer system in which the individual gas analyzer benches are detachable and house their own electronics. Such a design will allow the benches to be interchanged with any host monitor and eliminate the risk of distortion and noise affects due to external transmission lines. It is also desirable that such interchangeable benches be capable of storing their respective calibration characteristics and of providing such information to the corresponding host unit.

The prior art systems disclosed in U.S. Pat. Nos. 4,859,858, 4,859,859 and 4,194,720 further disclose a manner of engaging the gas analyzer bench with the sample cell using detents and complementary recesses. A spherical detent and spring detent combination is disposed in a bore in the bench housing. The spherical detent can be trapped in one of four complementary recesses in the center section of the sample cell casing so that the bench may be coupled thereto in any one of several orientations. The purpose of this design is to facilitate engagement of the bench and cell by reducing the precision needed to assemble them.

A drawback of the prior art design is that the movement of the detents results in wear on the casing which may eventually lead to enlarged recesses making the fit between the bench and cell less secure. The likelihood of this is even greater when metal parts (e.g., spring detents) are used with a plastic casing. A loose fit could lead the optical beam path to drift resulting in less accurate $CO_2$ measurements. It is therefore desirable to design a gas analyzer system having a bench-sample cell mating configuration that does not lead to component wear.

Many prior art devices, including the gas analyzer disclosed in 5,092,342, employ an incandescent lamp as the source of infrared radiation. An incandescent lamp is desirable as an infrared source in that it is relatively inexpensive and has a rapid decay time and low power requirements. However, a drawback of the incandescent lamp is that it is not very rugged and therefore susceptible to failure if dropped. It is therefore also desirable to design a gas analyzer system having a low cost infrared radiation source which is both rugged and has good operating characteristics.

It is therefore an object of the present invention to provide an apparatus and method for carbon dioxide measurement which improves upon the prior art.

It is also an object of the present invention to provide an apparatus for carbon dioxide measurement which employs a lens-free gas analyzer bench design so as to increase accuracy of the carbon dioxide measurement.

It is also an object of the present invention to provide an apparatus for carbon dioxide measurement having improved thermal stability.

Another object of the present invention is to provide an apparatus for carbon dioxide measurement having a dual heating control system for independently controlling the temperature of the detector assembly and sample cell windows.

Another object of the present invention is to provide an apparatus for carbon dioxide measurement which shuts off the heating control system if the system malfunctions.

It is also an object of the present invention to provide an apparatus for carbon dioxide measurement in which a gas analyzer bench is provided which is detachable and interchangeable with all compatible host units.

It is also a further object of the present invention to provide an apparatus for carbon dioxide measurement with interchangeable benches each having stored calibration information so as to eliminate the need to calibrate the bench each time it is plugged into a host unit.

It is also a further object of the present invention to provide an apparatus for carbon dioxide measurement in which the gas analyzer bench can be assembled with the sample cell in a manner that reduces wear on the bench housing.

It is still a further object of the present invention to provide an apparatus for carbon dioxide measurement which employs an inexpensive infrared radiation source which is resilient to physical shock.

It is still a further object of the present invention to provide an apparatus for carbon dioxide measurement having integrated circuitry capable of accepting an electrical signal proportional in magnitude to the intensity of the infrared radiation received by a detection unit within the sensor and supplying an output indicative of the $CO_2$ concentration in a patient's respiratory gases continuously at the end tidal peak, during the inspired phase, and indicative of the patient's respiration rate.

A more general object of the present invention is to provide an apparatus for carbon dioxide measurement that is less expensive and lighter in weight than prior art devices.

SUMMARY OF THE INVENTION

The present invention provides a new and novel apparatus and method for the measurement of carbon dioxide which overcomes the drawback of prior art devices and methods, and achieves the aforesaid objects.

Accordingly, one aspect of the present invention is drawn to an apparatus for determining the concentration of a selected gas in a mixture of gases containing the selected gas and providing an electrical signal representative thereof. The apparatus comprises a housing, a sample cell supported in the housing for containing the gas mixture, source means mounted in the housing for emitting infrared radiation, measuring detector means for detecting infrared radiation passing through said sample cell at the characteristic absorption wavelength of the selected gas and providing an output signal representative thereof, reference detector means for detecting infrared radiation passing through the sample cell at a wavelength other than that of the characteristic absorption wavelength of the selected gas and providing an output signal representative thereof, optical means mounted in the housing for directing the radiation into a beam travelling down a beam path through the sample cell, and holder means formed in the housing for manually releaseably holding the sample cell in the beam path between the source means and a beam splitting means. The optical means has a reflector for forming a substantially collimated beam directed through the sample cell, beam splitting means for directing respective portions of the beam passing through the sample cell to the measuring detector means and the reference detector means, and a collector means associated with the measuring detector means and reference detector means for focusing the respective beam portions thereon.

The various features of novelty which characterize the invention are pointed out with particularity in the claims annexed to and forming a part of this disclosure. For a better understanding of the present invention and the advantages attained by its use, references are made to the accompanying drawings and descriptive matter in which the preferred embodiment of the invention is illustrated.

DETAILED DESCRIPTION OF THE PREFERRED EMBODIMENT

The present invention provides a new and novel gas analyzer and method for measuring dissolved blood gases by detecting carbon dioxide in respiratory gases present in a sample cell which is in series with the airway of a patient on a ventilator. The sample cell is removable and interchangeable and provides the gas analyzer optical access to the gases in the airway. The present invention overcomes the drawbacks of prior art devices and achieves the aforesaid advantages.

Figure 1:
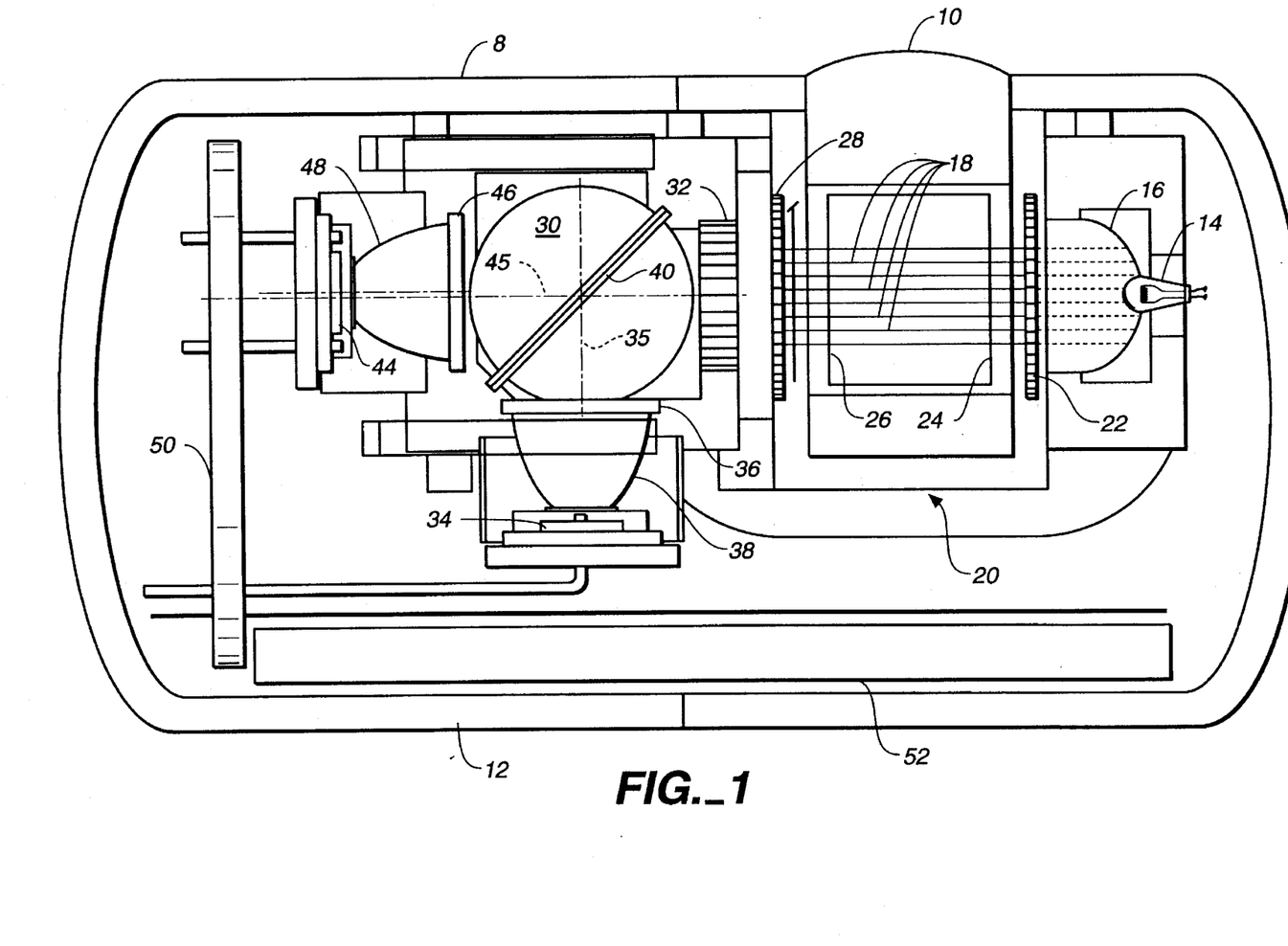
FIG. 1 shows a cross-sectional side view of the gas analyzer of the present invention.

Referring now to the drawings generally, wherein like numerals designate the same element throughout the several drawings, and to FIG. 1 in particular, there is shown a cross-sectional view of the gas analyzer of the present invention with which, as an example, the $CO_2$ content is detected in the respiratory air of a patient under anesthesia.

The gas analyzer 1 includes gas analyzer bench 8 and removable sample cell 10. Generally, gas analyzer bench 8 houses the optical, measurement and electronic control components of the analyzer. The optical components include an infrared radiation source emitter 14, a reflector 16 which defines and directs a beam of radiation through the sample cell 10 containing the respiratory gasses towards a beam splitter 40 which directs specific wavelengths of radiation 35 and 45 onto respective collectors 38 and 48 which in turn focus the respective portions 35 and 45 of the infrared radiation beam onto radiation detectors 34 and 44. The measurement components include detectors 34 and 44 which measure the intensity of radiation of the respective beams. These measurements are then sent in the form of electrical signals to a preamplifier 50 and then onto the control circuitry on hybrid board 52.

More specifically, gas analyzer bench 8 includes a housing or casing 12, wherein suitable source means, such as tungsten filament lamp 14, is configured as an infrared radiation source. Source 14 is used in a non-dispersive infrared (NDIR) technique well known to one of ordinary skill in the art. The radiation emitted by source 14 is reflected by a reflector, such as parabolic mirror 16. Source 14 is disposed near the focal point of parabolic mirror 16 so that the emitted infrared radiation is shaped to define a beam 18 of essentially parallel rays.

The collimated beam 18 travels along the path of an optical axis, leaving the reflector 16, exits housing 12 of the U-shaped holder portion 20 of bench 8 through a first holder window 22, enters the sample cell 10 through a corresponding first sample cell window 24, and interacts with the respiratory gas mixture present in sample cell 10. Carbon dioxide in the gas mixture absorbs infrared radiation with a wavelength of 4.26 microns. The attenuated beam exits the sample cell 10 through a second sample cell window 26, reenters bench 8 through second holder window 28 and enters detector assembly 30 via aperture 32.

Detector assembly 30 receiving beam 18 and provides an electrical signal representative of the intensity of the radiation received. Detector assembly 30 includes measuring detector 34 and reference detector 44, preferably of lead selenide material. Suitable means for splitting beam 18 into a measurement beam 35 and a reference beam 45, such as dichroic beam splitter 40, provides the radiation required for the measurement to detectors 34 and 44. Dichroic beam splitter 40 is made of a material which preferably deflects rays having a radiation wavelength in the range of 4.3 microns and alternately transmits wavelengths in the range of 3.7 microns, for example. The $CO_2$ to be detected is sensitive to the measuring wavelength of approximately 4.3 microns so that the absorption of the $CO_2$ is a measure of the concentration thereof. On the other hand, the radiation of the reference wavelength of 3.7 microns is not influenced by the $CO_2$.

The deflected beam 35, which is used as a measurement beam, is directed along a path situated at a right angle to the direction of the collimated beam 18 as indicated. The transmitted beam 45, which is used as the reference beam, is permitted to pass through beam splitter 40 and impinge upon reference detector 44. Measurement beam 35 passes through a measurement filter 36 and reference beam 45 passes through a reference filter 46 to provide a further precise determination of the measuring and reference wavelength ranges, respectively. Each of beams 35 and 45 then enter into respective parabolic optical collectors 38 and 48 which focus beams 35 and 45 onto measurement detector 34 and reference detector 44, respectively.

The signals produced by the measurement detector 34 and reference detector 44 are sent to a preamplifier, located on preamplifier circuit board 50, then to a multiplexer, located on hybrid board 52 (see FIG. 3), and to a signal processing board (not shown), commonly used by those skilled in the art, which then ratios the two signals to produce an output signal indicative of the concentration of $CO_2$ in the gas mixture under investigation. Also, other information can be extracted from the signal.

In medical applications, the present invention provides for processed $CO_2$ data to report maximum and minimum $CO_2$ concentrations from 0.0 to 100.0 Torr with a 0.1 resolution and an overall range from −5.0 to 120.0 Torr. Negative gas concentrations are reported in order to indicate negative drift. Furthermore, $CO_2$ concentrations are continuously measured at a rate of 6.25 milliseconds and transmitted to the host system in multiples of two, four, etc. measurement data packets. End-tidal $CO_2$ measurements are determined by tracking the peak unfiltered data between the first excursion of the filtered data through the upper threshold from below and the first excursion of the filtered data through the lower threshold from above. The end-tidal measurement is further processed by tracking the peak end-tidal with a 5 second averaging window. From this averaging window, the average breath-to-breath duration is calculated. The respiratory rate is then computed as the inverse of this average.

In order to optimize operating conditions of the present invention, a novel dual heating control system is used to stabilize the temperature of the sensor block and of the sample cell independently of each other. The heating control system is composed of two heating servos, or closed loop feed back control systems, one for the sample cell windows and one for the detector block. The dual-servo design eliminates the effects of variations in ambient temperature and sample cell flow rate on the detector block temperature so as to increase the accuracy of the detector measurements. In this way, the temperature of the system can be fine-tuned allowing it to perform more accurately. The detectors, in particular, would be best served by independently controlled heating as these components are the most sensitive to ambient temperature fluctuations.

Figure 2:
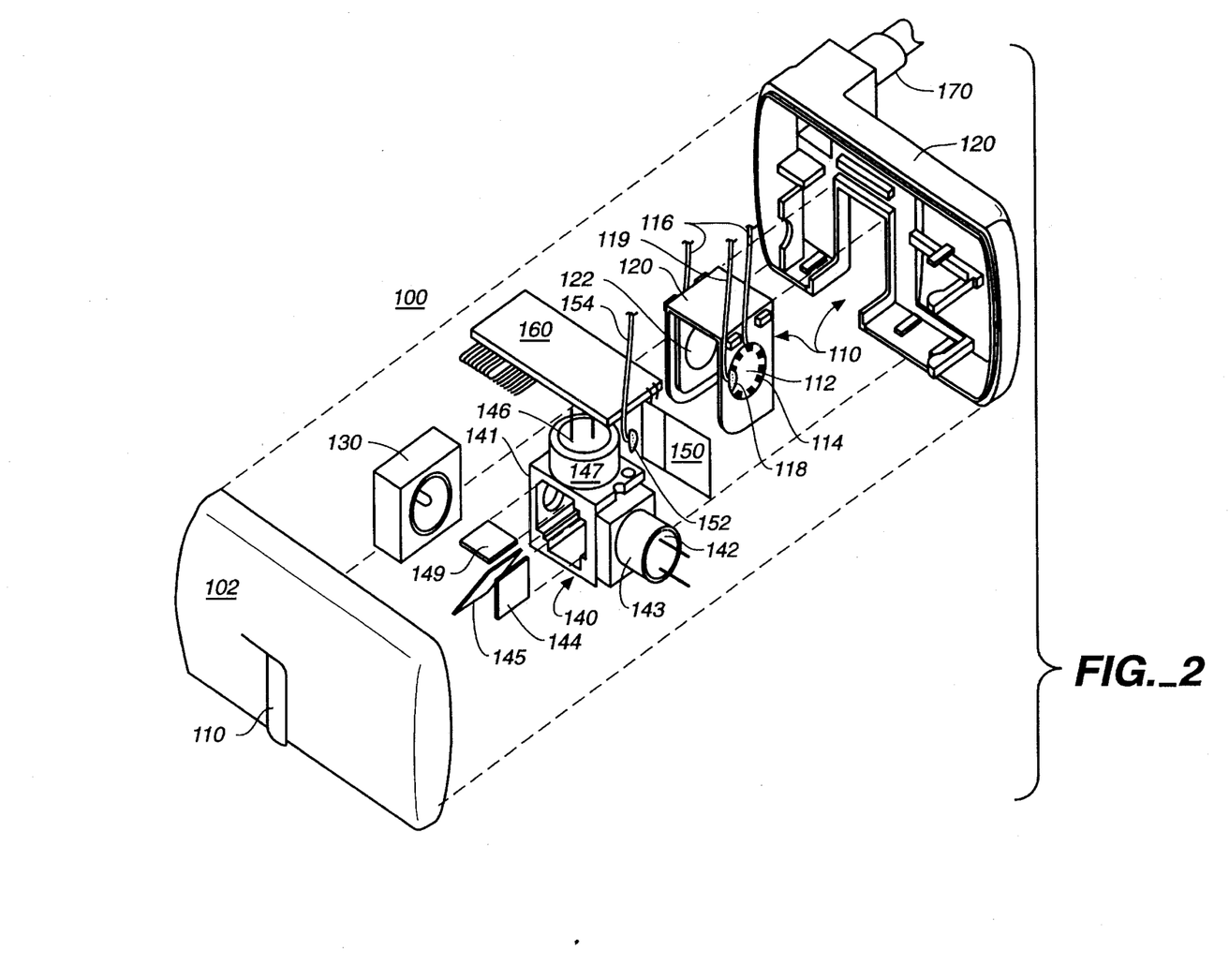
FIG. 2 provides an exploded isometric view of the gas analyzer of the present invention.

Referring now to FIG. 2, there is shown an exploded isometric view of the gas analyzer of the present invention which illustrates the novel temperature control system. Each of the two heating servos includes heating means and a temperature sensor which feeds back the temperature of the heated component to heater control circuitry. The amount of heat applied by the heating means can then be adjusted.

Figure 3:
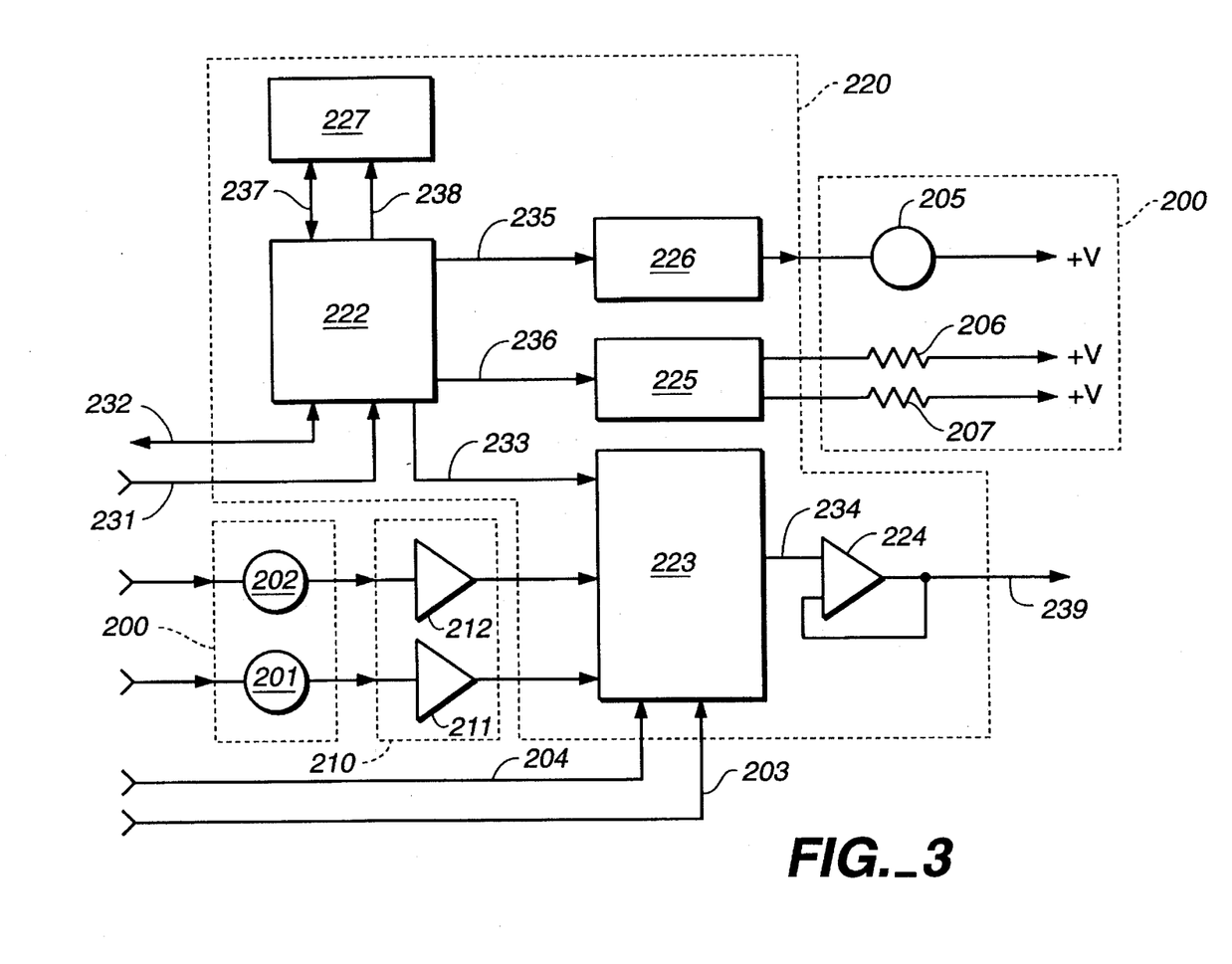
FIG. 3 shows a block diagram of the electronic circuitry housed within the gas analyzer of the present invention.

More specifically, the gas analyzer 100 has bench housing 102 which encases removable sample cell 120, source emitter unit 130, detector block assembly 140, and hybrid board 160 (see FIG. 3). Formed in the housing 102 is holder 110 which holds sample cell 120 in position within the gas analyzer bench. Holder windows 112 (only one window is shown) are seated transmissive to the infrared radiation beam emitted by source emitter unit 130 and so as to be flush with corresponding sample cell windows 122 (only one window is shown).

Suitable heating means 114 is provided on the surface of each of the holder windows 112 and facing away from sample cell 120 for applying heat to corresponding sample cell windows 122. In the preferred embodiment, the heating means consists of ring-shaped heating tracks 114 and made of a thick-film set of resistors that are bonded onto the periphery of the windows 112 with wires 116 soldered to the ends of the heating track 114 for providing an electric current therethrough. The resistors can be applied using thick film technology, for example, a technique commonly known to those skilled in the art. Heating element tracks 114 are arranged along the circumference of windows 112 so as to leave an unobstructed path for a radiation beam to pass through.

The windows 112 are made of a material having good heat conductivity such as sapphire. With the sample cell 120 seated in place, the windows 112 are in "thermal contact" (although not physical contact) with the sample cell windows 122. In this way, thermal energy flows to the sample cell 120, its temperature being maintained above the condensation point of water vapor, thereby preventing fogging of the windows and absorption and dispersion of the infrared beam.

Also included as part of the window cell heating servo is a suitable means for sensing the temperature of the sample cell windows 122. In the preferred embodiment, the temperature sensor consists of a thermistor 118 positioned on the surface of the holder window 112 closest to the detector block 140. The thermistor 118 provides a feedback signal, via wires 119, to the hybrid board 160 which regulates the current provided to the window heater tracks 114.

The detector block assembly 140 also has a heating servo which is independent of the window heating servo. Detector block assembly 140 includes detector block 141, measurement detector 142, measurement collector 143, measurement filter 144, dichroic beam splitter 145, reference detector 146, reference collector 147, and reference filter 148. A strip heater 150, preferably of Capton tape having a resistive element, is positioned flush against one of the detector block walls made of thermally-conductive material, such as aluminum. The window 112 adjacent to detector block 141 receives heat by convection from the detector block 141 in addition to its own heating element 114. The temperature in the detector block 141 is measured and regulated by means of a thermistor 152 embedded therein. In this way, the thermistor 152 provides a feedback signal, via wires 154, to the hybrid board 160 which also regulates the current provided to the strip heater 150. Cable 170 caries power, data and clock lines to and from the signal processor and power control boards of the system.

Accordingly, the dual heating servos regulate the condensation on the sample cell windows as well as the ambient temperature surrounding the gas analyzer while the analyzer emits radiation, detects the radiation into a beam, expose the respiratory gases in the sample cell to the beam of radiation, splits the beam into the two beams having preselected wavelengths, and filters, collects, and detects these respective beams at a predetermined temperature.

The situation may arise where the feedback signal from one or both of the heater control system thermistors is not an accurate reading of the actual temperatures being measured. This may be due to a thermistor whose soldering has become loose or to a latent manufacturing defect in the thermistor. To protect against such a condition, the present invention employs an energy-temperature safety algorithm which determines if the temperature response of the heating system is within a predetermined spectrum for a given range of energy added to the system. In other words, the thermistor temperature output values are checked against an expected band of values for a given voltage or current input. If the temperattire rise of the system is not within a predicted band, the processor on the hybrid board sends a command to the signal processor to turn off the heaters.

As will be discussed below, the thermal response of the gas analyzer system of the present invention is defined by a characteristic equation. The temperature characterization constants for each gas analyzer unit are stored in the memory circuitry of its hybrid board. In this way, the temperature response of the heater control system can be continuously monitored.

Another aspect of the present invention is that it provides for universal gas analyzer-host system compatibility, i.e., every gas analyzer assembly will work with any host unit. Interchangeability of the gas analyzers of the present invention is accomplished by storing and providing information characterizing the unique performance of the infrared source and detectors for each gas analyzer within the analyzer unit itself. This calibration data is stored in a nonvolatile random access memory (NVRAM) chip located on the hybrid board within the gas analyzer housing, which also drives the window and block heaters and the source lamp as well as transmits data from the detectors and thermistors. When a gas analyzer of the present invention is plugged into the host system, the stored calibration data is sent to the signal processor and communicated to the host unit.

In addition to the electronic circuitry, including a hybrid board, housed within the gas analyzer of the present invention are a signal processor board and a power conversion board used to manage data and communicate with the host unit which displays the desired information for the user. The hybrid board contains circuitry that drives the window and block heaters as well as the infrared source lamp. Additionally, it stores and reports calibration data and transmits data from the detectors and thermistors. The power conversion board provides all necessary voltages for the operation of the present invention including reference voltages for the hybrid and signal processor boards. The signal processor board supervises power distribution from the power conversion board, initializes and regulates all heating functions, collects, processes and reports $CO_2$ levels from the gas analyzer, communicates with the host system, and monitors and reports system failures and errors.

Referring now to FIG. 3, a block diagram is drawn of the electronic circuitry located within the gas analyzer housing, specifically, components not incorporated on a circuit board 200, a preamplifier board 210 and a hybrid board 220. The components not included on any circuit board are the measurement and reference detectors 201 and 202, respectively, the system temperatures 203 provided by the temperature sensors of the heating servos, the infrared source lamp 205, and the detector block and window heaters, 206 and 207, respectively. Preamplifier board 210 contains amplifiers 211 and 212 which amplify the detector signals to a level acceptable by hybrid board 220. In addition to the amplified detector signals, hybrid board 220 receives temperature signals 203 generated from window and detector block temperature sensors (not shown) and receives system voltages 204 provided by a power control board (not shown), such as a 10 volt reference voltage and a ground voltage. Hybrid board 220 provides outputs which drive the window and block heaters 206 and 207, respectively, as well as the infrared source lamp 205. Additionally, hybrid board 220 outputs a data line 239 which sends data to be processed by the signal processing board (not shown).

More specifically, FIG. 3 depicts hybrid board 220 incorporating microprocessor 222, multiplexer 223, postamplifier 224, voltage driver 225, voltage-controlled current source 226, and NVRAM 227. Microprocessor 222 communicates with the signal processor via clock line 231 and bi-directional serial data line 232. Processor 222 is responsible for time division multiplexing of data from the measurement and reference detectors 201 and 202, respectively, the system temperatures 203 and the system voltages 204. This is accomplished via clock line 233. A multiplexed output signal 234 is amplified postamplifier 224 and then provided to the signal processor. Voltage control signal 235 is provided by microprocessor 222 for operating voltage controlled current source 226 which in turn drives source lamp 205 with a current pulse of 40 Hz with a duty cycle of 25%. In addition, processor 222 provides a control line 236 for voltage driver 225 which drives the block heater 206 and window heater 207. The calibration constants of the particular gas analyzer as well as unit identifiers (i.e., serial numbers) are provided to NVRAM 227 via bi-directional serial data line 237 and clock line 238. NVRAM 227 stores this information until required for initializing a host system.

The calibration procedure of the present invention first requires correlating the gas concentration of a gas sample introduced into the sample cell with the amount of radiation that is impinged on the measurement and reference detectors, represented as a ratio of the two detector signals. A polynomial equation is then derived with coefficients characterizing each optical component, i.e., radiation source, measurement detector and reference detector. The coefficients of the characteristic equation are then stored in the NVRAM.

The calibration process also defines the "zero point" of the system, that is, the signal level which corresponds to zero concentration of the gas under investigation. This "zero point" is known to be a function of the temperature of the optical components and is stored in the NVRAM as a constant of the characteristic polynomial equation. In addition, the temperature behavior of the gas analyzer is also characterized with its corresponding coefficients being stored in the NVRAM. Temperature calibration will allow the system to operate at temperatures above 40° C. within a relaxed accuracy band.

After initial calibration of a gas analyzer unit, it will be necessary to periodically determine whether the unit has maintained its original performance characteristics or whether the unit requires recalibration. To this end, the present invention provides an auxiliary span check filter. The span check filter is an optical device which is positioned in the gas analyzer housing in lieu of a sample cell. The span check filter simulates a known concentration of $CO_2$, for example, by generating a differential transmission of infrared radiation on the measurement and reference detectors. By means of a span check software algorithm stored on the signal processing board and initiated by a user command, the reported concentration of $CO_2$ from the detectors is compared against a band of acceptable values for $CO_2$ concentration. If the reported $CO_2$ value is out of the band specification, the gas analyzer requires recalibration.

Figures 4, 5, 7:
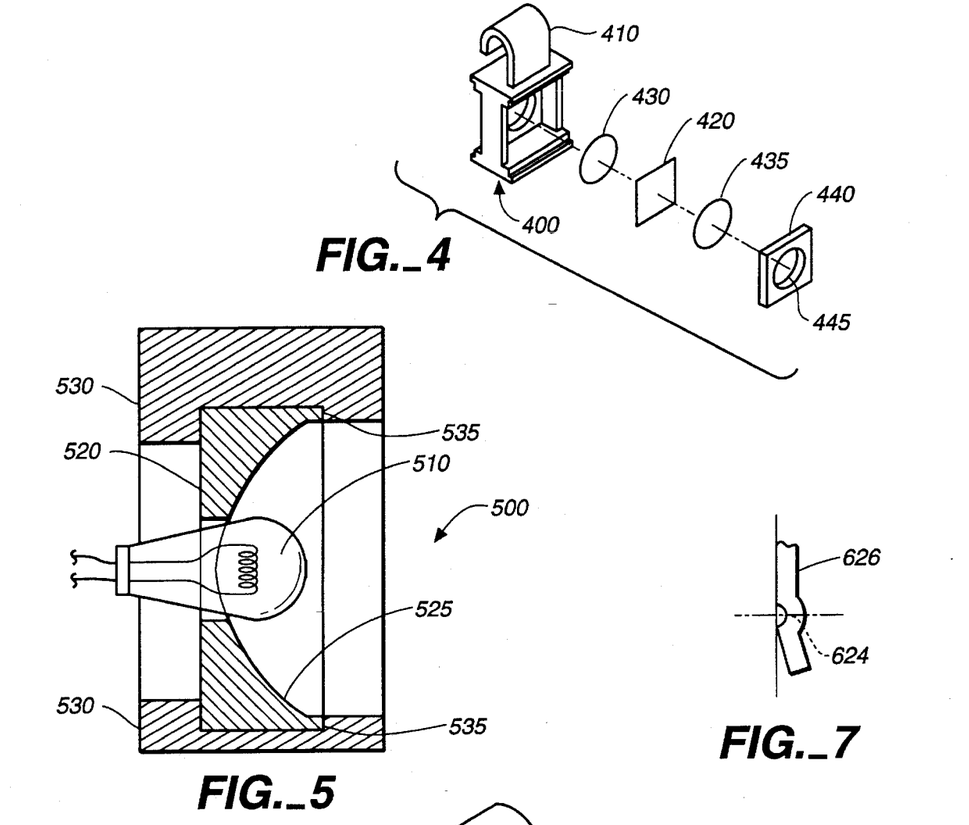
FIG. 4 shows an exploded isometric view of the span check filter of the present invention.
FIG. 5 shows a cross-sectional side view of the infrared radiation source of the present invention.
FIG. 7 provides an enlarged front view of a detent of the mating configuration depicted in FIG. 6.

Referring now to FIG. 4, a span check filter of the present invention is provided. The span check filter 400 has holder 410 which encases filter 420 sandwiched between two windows 430 and 435, preferably made of sapphire. A cover 440 having a window 445 is aligned with and flush against window 435. When positioned in a gas analyzer, cover 440 is juxtaposed against and flush with the aperture leading to the detector assembly.

The present invention employs a tungsten filament lamp, a type of incandescent lamp, as means for the infrared radiation source. The tungsten filament lamp is chosen for its low cost, rapid decay time and low power requirements. In the field of use, it is common for a gas analyzer to be dropped or inadvertently subject to shock loads. A typical drop of three feet results in shock loads in excess of 3000 G that are imparted to the filaments of the tungsten lamp. These shock loads will cause the filaments to either fuse or rupture which can result in failure of the source. In order to prevent the above deleterious affects, the present invention employs an elastomeric shock absorbing system. The shock absorber also maintains optical alignment of the source.

Referring now to FIG. 5, a side elevation view is shown of the infrared radiation source lamp of the present invention. The source emitter unit 500 includes a tungsten filament lamp 510 seated in reflector 520 having parabolic mirror 525. Reflector 520 is seated in annular recess 535 of shock absorber 530 having an annular design and preferably made of neoprene.

Figure 6:
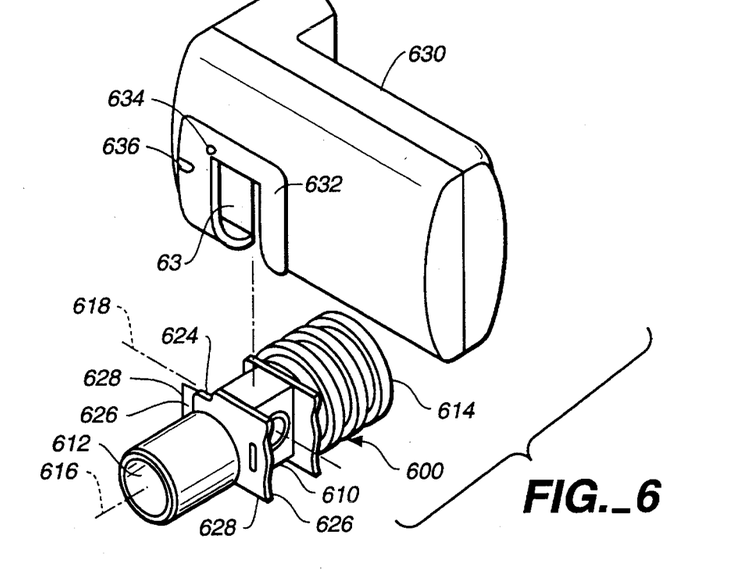
FIG. 6 provides a perspective view of the gas analyzer and sample cell having a the detent-recess mating configuration according to one embodiment of the present invention.

Turning now to FIG. 6, an embodiment of the gas analyzer system of the present invention is depicted having a detent-recess mating system for securing the coupling of a gas analyzer with an airway adapter. Airway adapter 600 with sample cell 610 is to be connected in series with the airway of the a patient by means of tubes (not shown) attached to ends 612 and 614. When sample cell 610 is seated within holder portion 638 of gas analyzer 630, the airway runs along axis 616 transversely to the directional axis 618 of the infrared radiation beam.

Gas analyzer 630 has a large recess 632 in its housing, made of plastic, to accommodate airway adapter 600. Located on the surface of large recess 632 is raised detent 634 molded. To couple airway adapter 600 to gas analyzer 630, sample cell 610 is positioned within holder portion 638 of gas analyzer 630. As airway adapter 600 is pushed into place, detent 634 and corresponding recess 624, molded into the casing of sample cell 610, are firmly juxtaposed against each other.

Still referring to FIG. 6, a second detent-recess pair is depicted by detent 626 on flange 628 of sample cell 610 and corresponding recess 636 molded in the housing of gas analyzer 630. Again, when airway adapter 600 is pushed into place within gas analyzer 630, detent 628 becomes firmly juxtaposed against recess 636.

Referring now to FIG. 7, an enlarged side view is shown of flange 628 having raised detent 626. When sample cell 620 is inserted within gas analyzer 600, the "dog leg" design of flange 628 acts as a spring-loaded force securing detent 626 within recess 636.

The molded detent-recess mating system of the present invention eliminates wear on the casing by engaging the gas analyzer with a sample cell without employing any discrete or movable parts.

It is understood that the foregoing description is that of the preferred embodiments of the invention and that various changes and modifications may be made thereto without departing from the spirit and scope of the invention as defined in the appended claims.

What is claimed is:

1. An apparatus for determining the concentration of a selected gas in a mixture of gases containing the selected gas and providing an electrical signal representative thereof, comprising:

a housing;

a sample cell supported in said housing for containing the gas mixture;

source means mounted in said housing for emitting infrared radiation;

measuring detector means for detecting infrared radiation passing through said sample cell at the characteristic absorption wavelength of the selected gas and providing an output signal representative thereof;

reference detector means for detecting infrared radiation passing through said sample cell at a wavelength other than that of said characteristic absorption wavelength of the selected gas and providing an output signal representative thereof;

lenseless optical means mounted in said housing for directing said radiation into a beam traveling down a beam path through said sample cell, said optical means comprising a reflector for forming a substantially collimated beam directed through said sample cell and further comprising dichroic beam splitting means for directing a portion of said collimated beam having a bandwidth including said characteristic absorption wavelength to said measuring detector means and for directing a portion of said collimated beam having a bandwidth not including said characteristic absorption wavelength to said reference detector means, said optical means further comprising first and second collector means positioned, respectively, adjacent to each of said measuring detector means and said reference detector means for reflectively focusing said respective beam portions thereon;

filter means associated with said measuring detector means for further limiting energy passing therethrough to said bandwidth including said characteristic absorption wavelength; and filter means associated with said reference detector means for further limiting energy passing therethrough to said bandwidth not including said characteristic absorption wavelengths.

2. The apparatus of claim 1 further comprising holder means formed in said housing for manually releaseably holding said sample cell in said beam path between said source means and said beam splitting means.

3. The apparatus of claim 1 wherein said source means comprises a tungsten filament lamp encased in a shock absorbing material.

4. The apparatus of claim 1 wherein said reflector is a parabolic mirror positioned so that said source means is located substantially at the focal point thereof.

5. The apparatus of claim 1 further comprising thermal regulation means for inhibiting condensate build-up within said sample cell and for minimizing variations in the ambient temperature surrounding said measuring detector means and said reference detector means.

6. An apparatus for determining the concentration of a selected gas in a mixture of gases containing the selected gas and providing an electrical signal representative thereof, comprising:

a housing;

a sample cell supported in said housing for containing the gas mixture, said sample cell having first and second windows positioned transversely to said beam;

source means mounted in said housing for emitting infrared radiation;

optical means mounted in said housing for directing said radiation into a beam traveling down a beam path through said sample cell;

measuring detector means for detecting infrared radiation passing through said sample cell at the characteristic absorption wavelength of the selected gas and providing an output signal representative thereof;

reference detector means for detecting infrared radiation passing through said sample cell at a wavelength other than that of said characteristic absorption wavelength of the selected gas and providing an output signal representative thereof;

holder means formed in said housing for manually releasably holding said sample cell in said beam path, said holder means having first and second windows corresponding to said first and second windows of said sample cell and positioned transversely to said beam, said first holder means window being positioned proximate and upstream of said first sample cell window, said second holder means window being positioned proximate and downstream of said second sample cell window;

window temperature regulation means, for inhibiting condensate build-up on said first and second sample cell windows, comprising window heating means for applying heat to said first and second sample cell windows and window temperature sensor means for monitoring the temperature of said sample cell, said window temperature sensor means providing an output signal indicative of said temperature to a temperature control means capable of increasing or decreasing the amount of energy provided to said window heating means so as to inhibit condensate build-up on said sample cell windows, wherein said window heating means comprises resistive elements attached to said first and second windows of said holder means and means for supplying a current to said resistive elements, and further wherein said window temperature sensor means comprises a thermistor mounted on said second window of said holder means; and detector temperature regulation means, for minimizing variations in the ambient temperature surrounding said measuring detector means and said reference detector means, comprising a thermally-conductive block in which said measuring detector means and said reference detector means are seated, block heating means for applying heat to said thermally-conductive block, comprising a heater strip of resistive material attached to the outside of a wall of said thermally-conductive detector block, and block temperature sensor means for monitoring the temperature of said block and for providing an output signal indicative of said block temperature to said temperature control means, said temperature control means being capable of increasing or decreasing the amount of energy provided to said block.

7. The apparatus of claim 6 further comprising shutoff means for turning off said window heater means when the value of said output signal indicative of said window temperature is outside a selected band of temperature values for the energy provided to said window heater means.

8. The apparatus of claim 6 wherein said block temperature sensor comprises a thermistor embedded in said thermally-conductive block.

9. The apparatus of claim 6 wherein said thermally-conductive block is composed of aluminum.

10. The apparatus of claim 6 further comprising shutoff means for turning off said block heater means when the value of said output signal indicative of said block temperature is outside a selected band of temperature values for the energy provided to said block heater means.

11. For use with a signal processing system, an apparatus for determining the concentration of a selected gas in a mixture of gases containing the selected gas and providing an electrical signal representative thereof, comprising:

a housing;

a sample cell supported in said housing for containing the gas mixture, said sample cell having first and second windows positioned transversely to said beam;

source means mounted in said housing for emitting infrared radiation;

optical means mounted in said housing for directing said radiation into a beam travelling down a beam path through said sample cell;

measuring detector means for detecting infrared radiation passing through said sample cell at the characteristic absorption wavelength of the selected gas and providing an output signal representative thereof;

reference detector means for detecting infrared radiation passing through said sample cell at a wavelength other than that of said characteristic absorption wavelength of the selected gas and providing an output signal representative thereof;

holder means formed in said housing for holding said sample cell in said beam path between said source means and said receiver means;

calibration means mounted in said housing for storing characterization information characterizing the performance of said source means, said measuring detector means, and said reference detector means, wherein said calibration means provides electrical signals representative of said information to the processing system; and span check filter means, for determining whether said characterization information accurately represents the performance of said apparatus, comprising hardware means for simulating the radiation absorption characteristics of a selected gas concentration and software means for running a span check algorithm, wherein said hardware means comprises a holder with a first window, a filter, and a second window, and means for securing said first window, said filter and said second window within said holder, whereby said hardware means is supported in said housing in lieu of said sample cell, and further wherein said software means verifies whether the value of the detector output signals representative of said simulated selected gas concentration lies within a range of prescribed values representing said selected gas concentration.

12. The apparatus of claim 11 wherein said calibration means comprises memory means for storing said characterization information so as to enable said apparatus to interface with one of a plurality of processing apparatus.

13. The apparatus of claim 12 wherein said memory means comprises a non-volatile random accessible memory.

14. The apparatus of claim 11 further comprising thermal regulation means for inhibiting condensate build-up within said sample cell and for minimizing variations in the ambient temperature surrounding said measuring detector means and said reference detector means.

15. A method for measuring the concentration of carbon dioxide in a stream of respiratory gases and processing the measurement so as to provide the user with information indicative of an individual's respiratory status, comprising the steps of:

emitting radiation;

directing said radiation into a beam;

exposing said stream of gases to said beam of radiation;

splitting said beam into first and second component beams having preselected wavelengths;

filtering said first and second component beams;

collecting said first and second component beams;

detecting said first and second component beams;

measuring the intensity of radiation in said first and second component beams;

ratioing the measured values of said radiation in said first and second component beams;

providing an electrical signal indicative of the ratioed value to a processing apparatus, said ratioed value indicative of the concentration of carbon dioxide in said stream of respiratory gases; and processing said signal for providing the individual's respiratory rate and respiratory carbon dioxide concentration continuously at end-tidal peak and during the inspired phase to a host unit.

16. The method of claim 15 wherein the steps of emitting radiation, directing said radiation into a beam, exposing said stream of gases to said beam of radiation, splitting said beam into first and second component beams having preselected wavelengths, filtering said first and second component beams, collecting said first and second component beams, and detecting said first and second component beams are performed at a predetermined temperature.

* * * * *